United States Patent [19]

Baumann

[11] Patent Number: 5,066,810
[45] Date of Patent: Nov. 19, 1991

[54] 3,5-DIMETHYL-4-METHOXYPYRIDINE DERIVATIVES

[75] Inventor: Karl Baumann, Vienna, Austria

[73] Assignee: CL Pharma Aktiengesellschaft, Linz, Austria

[21] Appl. No.: 432,874

[22] Filed: Nov. 7, 1989

[30] Foreign Application Priority Data

Nov. 15, 1988 [AT] Austria ................................. 2789/88

[51] Int. Cl.⁵ ............................................ C07D 213/68
[52] U.S. Cl. .................................. 546/300; 546/301; 546/303
[58] Field of Search ......................... 546/300, 301, 303

[56] References Cited

U.S. PATENT DOCUMENTS

| | | | |
|---|---|---|---|
| 3,829,429 | 8/1974 | Clement | 546/300 |
| 4,159,382 | 6/1979 | Garrou | 546/329 |
| 4,255,431 | 3/1981 | Junggren et al. | 424/263 |
| 4,337,257 | 6/1982 | Junggren et al. | 424/263 |
| 4,472,409 | 9/1984 | Senn-Bilfinger | 424/263 |
| 4,508,905 | 4/1985 | Junggren et al. | 546/271 |
| 4,620,008 | 10/1986 | Brandstrom et al. | 546/271 |
| 4,739,057 | 4/1988 | Leone-Bay et al. | 546/303 |
| 4,785,113 | 11/1988 | Junek et al. | 546/345 |

OTHER PUBLICATIONS

Hilgetag et al., Ed. "Preparative Organic Chemistry", N.Y.: John Wiley & Sons, 1972, p. 342.
Buelta Casado et al., Chemical Abstracts, vol. 106, 102092f (1987).

Primary Examiner—Mary C. Lee
Assistant Examiner—Lenora Miltenberger
Attorney, Agent, or Firm—Wenderoth, Lind & Ponack

[57] ABSTRACT

A process for the preparation of compounds of formula I

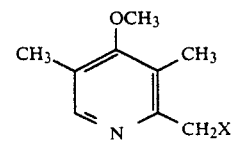

in which X is the radical OH or Cl, by the catalytic hydrogenation of 3,5-dimethyl-4-methoxy-2-cyanopyridine, subsequent reaction of the resulting 3,5-dimethyl-4-methoxy-2-aminomethylpyridine to give 3,5-dimethyl-4-methoxy-2-hydroxymethylpyridine and, if desired, chlorination to give 3,5-dimethyl-4-methoxy-2-chloromethylpyridine, and the novel intermediate 3,5-dimethyl-4-methoxy-2-aminomethylpyridine.

1 Claim, No Drawings

3,5-DIMETHYL-4-METHOXYPYRIDINE DERIVATIVES

The invention relates to a novel process for the preparation of 3,5-dimethyl-4-methoxy-2-hydroxymethylpyridine or 3,5-dimethyl-4-methoxy-2-chloromethylpyridine, to the novel intermediate, 3,5-dimethyl-4-methoxy-2-aminomethylpyridine, formed in this process and to the use of said intermediate.

3,5-Dimethyl-4-methoxypyridine derivatives are valuable intermediates for the preparation of ATPase inhibitors, as described for instance in U.S. Pat. No. 4,255,431, U.S. Pat. No. 4,337,257 and U.S. Pat. No. 4,508,905.

U.S. Pat. No. 4,472,409 discloses the preparation of 3,5-dimethyl-4-methoxy-2-hydroxymethylpyridine or 3,5-dimethyl-4-methoxy-2-chloromethylpyridine from 2,3,5-trimethylpyridine, the first step being to react this compound with $H_2O_2$ to give the N- oxide, after which this N-oxide is nitrated to give 2,3,5-trimethyl-4-nitropyridine N-oxide and the $NO_2$ group is exchanged for a methoxy group by treatment with sodium methoxide. The 2,3,5-trimethyl-4-methoxypyridine N-oxide formed is then treated with acetic anhydride, the resulting acetyl derivative is saponified to give 3,5- dimethyl-4-methoxy-2hydroxymethylpyridine and, if desired, the latter is reacted with thionyl chloride to give 3,5-dimethyl-4-methoxy-2-chloromethylpyridine.

Further U.S. Pat. No. 4,620,008 discloses another process whereby 1,4-dimethoxy-3,5-dimethylpyridinium methylsulphate is obtained first by reacting 3,5-dimethyl-4methoxypyridine N-oxide, prepared as described in U.S. Pat No. 4,472,409 with dimethylsulphate, and 3,5-dimethyl-4-methoxy-2- hydroxymethylpyridine is then obtained by rearrangement.

The starting compound for these processes, 2,3,5-trimethylpyridine, is obtainable only with difficulty and in poor yield, for instance by reacting 3,5-dimethylpyridine with methyl-lithium at low temperatures.

U.S. Pat. No. 4,785,113 discloses the preparation of the title compounds from ethyl 2-methylacetoacetate by reaction with $NH_3$ to give ethyl 3-amino-2-methylcrotonate, reaction with diethyl monomethylmalonate to give 2,3,5-trimethyl-4,6-dihydroxypyridine, chlorination to give 2,4-dichloro-3,5,6-trimethylpyridine, selective cleavage of the 2-Cl substituent and exchange of the 4-Cl substituent for a methoxy group, and then oxidation to give the N-oxide. The subsequent reactions are carried out analogously to the process described in U.S. Pat. No. 4,472,409.

In this process, the 2,3,5-trimethyl-4-methoxypyridine N-oxide required for the rearrangements to modify the methyl group bonded in the 2-position has to be prepared from aliphatic compounds in a complicated 7-step process.

It has now been possible to find a simple process for the preparation of 3,5-dimethyl-4-methoxy-2-hydroxymethylpyridine or 3,5-dimethyl-4-methoxy-2-chloromethylpyridine from 3,5-dimethyl-4-methoxy-2-cyanopyridine, which is described in Chemical Abstracts, vol. 106, 1020928 (1987).

The invention accordingly relates to a process for the preparation of compounds of formula I

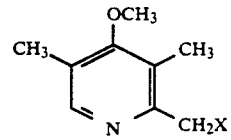

in which X is the radical OH or Cl, comprising catalytical hydrogenation of 3,5-dimethyl-4-methoxy-2-cyanopyridine of formula II

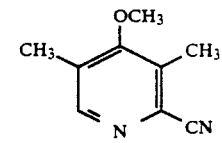

in the presence of an inert diluent, the resulting 3,5-dimethyl-4-methoxy-2-aminomethylpyridine of formula III

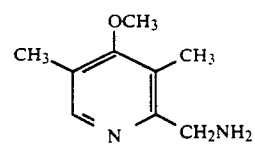

being then reacted with sodium nitrite in aqueous-acidic solution to give 3,5-dimethyl-4-methoxy-2-hydroxymethylpyridine and, if desired, the latter being then reacted with thionyl chloride to give 3,5-dimethyl-4-methoxy-2-chlormethylpyridine.

The intermediate formed in this process, 3,5-dimethyl-4-methoxy-2-aminomethylpyridine, is novel and represents a further subject of the invention.

The starting material for this process, 3,5-dimethyl-4-methoxy-2-cyanopyridine, can be prepared in a simple manner from 3,5-dimethylpyridine by oxidation to give 3,5-dimethylpyridine N-oxide, nitration and reaction with dimethyl sulphate to give 1,4-dimethoxy-3,5-dimethylpyridinium methylsulphate, treatment with KCN and subsequent exchange of the nitro group for a methoxy group with sodium methoxide.

In a first step, the cyano group is hydrogenated to the aminomethyl group. The hydrogenation is carried out in the presence of a hydrogenation catalyst and a diluent which is inert under the reaction conditions.

Examples of catalysts which can be used are Raney nickel or Pd on active charcoal. To prevent the formation of the secondary amine, it is preferred to add a base, such as $NH_3$, or an acid, for example a mineral acid or toluenesulphonic acid, up to 2 equivalents being used in the case where an acid is added.

It is preferred to use Raney nickel in combination with $NH_3$ or Pd/C in combination with an acid, Raney nickel with $NH_3$ being especially preferred.

Examples of suitable diluents which are inert under the reaction conditions are alcohols, such as methanol or ethanol, ethers, such as dioxane or tetrahydrofuran, or mixtures of diluents with water. Methanol is preferably used. Depending on the other reaction conditions, the hydrogenation takes place at about 20°–100° C., preferably at room temperature, and under a pressure of about 1 to 5 bar, preferably at normal pressure.

When the reaction is complete, the catalyst is filtered off and the solvent is removed in order to isolate the intermediate formed in the hydrogenation, 3,5-dimethyl-4-methoxy-2-aminomethylpyridine. The remaining residue can be purified further by conventional methods, for example by vacuum distillation, and crystallized.

The reaction of the novel intermediate to give 3,5-dimethyl-4-methoxy-2-hydroxymethylpyridine is carried out by diazotization of the amino group under hydrolyzing conditions.

The reaction is carried out in aqueous-acidic solution. Suitable acids are mineral acids or acetic acid. The acid used is preferably glacial acetic acid. The ratio of water to acid can vary within wide limits and is preferably about 9:1 to 1:1. The diazotization is carried out with sodium nitrite, it being possible for the sodium nitrite to be used in solid form or in solution. The reaction is carried out in the temperature range from about $-20°$ to $50°$ C., preferably from about $-5°$ to $10°$ C.

When the reaction is complete, the aqueous solution is rendered alkaline, the product is extracted with an organic solvent, for example methylene chloride, and the organic phase is dried.

The product is isolated by filtration of the organic phase and purified, for example by bulb-tube distillation.

If desired, the 3,5-dimethyl-4-methoxy-2-hydroxymethylpyridine prepared in this way is then reacted with thionyl chloride to give 3,5-dimethyl-4-methoxy-2-chloromethylpyridine.

The reaction is carried out in the presence of a diluent which is inert under the reaction conditions, for example in dichloroethane, methylene chloride, chloroform, dioxane or tetrahydrofuran.

Depending on the other reaction conditions, the reaction is carried out in the temperature range from about $-30°$ to $50°$ C., preferably from about $-20°$ to $0°$ C.

When the reaction is complete, the diluent is evaporated off, the residue is digested, for example in i-propanol, and 3,5-dimethyl-4-methoxy-2-chloromethylpyridine hydrochloride is isolated.

The process is preferably carried out starting from 3,5-dimethyl-4-methoxy-2-cyanopyridine, but without isolation of the intermediates up to 3,5-dimethyl-4- methoxy-2-chloromethylpyridine.

In this process, the catalyst is filtered off after the hydrogenation and the diluent is removed. The residue is then taken up in aqueous-acidic solution and the diazotization is carried out under hydrolyzing conditions.

The 3,5-dimethyl-4-methoxy-2-hydroxymethylpyridine which is present in an organic solvent after the extraction is then reacted with thionyl chloride to give 3,5-dimethyl-4-methoxy-2-chloromethylpyridine, which is isolated as described above.

The process affords a good total yield. In general, yields of 40–50% are achieved, based on 3,5- dimethyl-4-methoxy-2-cyanopyridine.

EXAMPLE 1

3,5-Dimethyl-4-methoxy-2-aminomethylpyridine

A mixture of 20 g of Raney nickel and 20 g of 3,5-dimethyl-4-methoxy-2-cyanopyridine in 650 ml of $NH_3$-saturated methanol, prepared by the passage of dry $NH_3$ gas, was hydrogenated for 3 days at room temperature and normal pressure. After flushing with Ar, the catalyst was filtered off and the solvent was removed on a rotary evaporator. The remaining violet-coloured liquid residue was purified by bulb-tube distillation.

T: $120°$ C. air bath temperature, p: 0.05 bar 13.5 g (65.9% of theory) of the title compound were obtained as a colourless oil.

$^1$H NMR (300 MHz/TMS)

(ppm) = 1.94 (sb, 2H, $-NH_2$), 2.21 (s, 3H, $-CH_3$), 2.24 (s, 3H, $-CH_3$), 3.75 (s, 3H, $-OCH_3$), 3.90 (s, 2H, $-CH_2$), 8.21 (s, 1H, pyr-H)

EXAMPLE 2

3,5-Dimethyl-4-methoxy-2-hydroxymethylpyridine

A solution of 3.61 g of $NaNO_2$ in 20 ml of $H_2O$ was added in portions, at $0°$ C., to a solution of 2.9 g of 3,5-dimethyl-4-methoxy-2-aminomethylpyridine in 50 ml of 10% aqueous acetic acid and the mixture was stirred for 1 h. It was then partitioned between 30 ml of 4 N NaOH and 50 ml of $CH_2Cl_2$, the organic phase was separated off and the aqueous phase was extracted again with 3 times 50 ml of $CH_2Cl_2$. The combined organic phases were dried over $Na_2SO_4$, filtered and evaporated. The brown crystalline crude product was purified by bulb-tube distillation.

T: $115°–135°$ C. air bath temperature, p: 0.01 bar 2.57 g (88.3% of theory) of the title compound were obtained as a colourless oil, which solidifies at room temperature.

$^1$H NMR (300 MHz/TMS/CDCl$_3$)

(ppm) = 2.12 (s, 3H, CH$_3$), 2.26 (s, 3H, CH$_3$), 3.77 (s, 3H, OCH$_3$), 4.62 (2, 2H, $-CH_2-$), 4.9 (sb, 1H, $-OH$), 8.19 (s, 1H, pyr-H)

EXAMPLE 3

Preparation of the starting compound, 3,5-dimethyl-4-methoxy-2-cyanopyridine a) 3,5-Dimethylpyridine N-oxide 98 ml of glacial acetic acid were added dropwise, at $25°$ C., to 350 g of 3,5-dimethylpyridine. The mixture was heated to $50°$ C. and 870.3 g of 40% peracetic acid were metered in such that the temperature could be kept at $50°$ C. by cooling. About 1 hour after the addition of the peracetic acid had ended, the reaction mixture was cooled to $25°$ C. and 230 g of $Na_2SO_3$ in 1 l of water were added dropwise, with cooling. After the excess peracetic acid had been destroyed (KI-starch test), 1330 ml of water were added, the mixture was rendered alkaline with 730 ml of 50% NaOH and the solution was extracted in several portions with a total of about 4500 ml of chloroform. The combined organic phases were dried with $Na_2SO_4$ and the solvent was evaporated off to about 740 ml.

b) 3,5-Dimethyl-4-nitropyridine N-oxide

The solution obtained from a) was added dropwise to 577.5 ml of concentrated sulphuric acid at a temperature of $40°$ C. and a pressure of about 0.26 bar, the solvent being stripped off at the same time. The solution was subsequently kept at $45°$ C. for 1 h under a water-jet vacuum and then heated to $70°$ C. and 577.5 ml of fuming $HNO_3$ were added dropwise, with cooling, such that the temperature did not exceed $80°–85°$ C. The mixture was left to cool overnight and added dropwise to a mixture of 3 kg of ice and 2 l of water, with cooling. The resulting mixture was then rendered alkaline with about 720 ml of 50% NaOH and extracted in several portions with about 9 l of chloroform. The combined organic phases were dried with $Na_2SO_4$ and concentrated to about 900 ml, 500 ml of diisopropyl ether were added at room temperature and the precipitate formed was filtered off and dried to give 427 g (77.7% of theory) of the title compound. M.p.: 180°–183° C. (subl.)

c) 1,4-Dimethoxy-3,5-dimethylpyridinium methylsulphate 4050 ml of ethyl acetate, 400 g of the product from b) and 390 g of dimethyl sulphate were refluxed for 4 h, cooled overnight and extracted in several portions with about 1600 ml of water.

d) 3,5-Dimethyl-4-nitro-2-cyanopyridine 464.9 g of KCN were dissolved in 3500 ml of water, the solution was cooled to 5° C and 1600 ml of the aqueous solution from c) were added dropwise, with cooling. About 1 h after the dropwise addition had ended, the precipitate was filtered off, washed with water and dried over $P_2O_5$ to give 377.4 g of the title compound (89.3% of theory, based on b). M.p.: 66°–71° C. $^1$H NMR (300 MHz/TMS/CDCl$_3$)

(ppm) = 2.40 (s, 3H, CH$_3$), 2.53 (s, 3H, CH$_3$), 8.59 (s, 1H, pyr-H)

e) 3,5-Dimethyl-4-methoxy-2-cyanopyridine 350 g of the product from d) were dissolved in 2100 ml of methanol, the solution was heated to the reflux temperature and a solution of 391 g of NaOCH$_3$ in 1500 ml of methanol was added dropwise. When the reaction was complete, 10 g of active charcoal were added, the mixture was cooled to 30° C. and filtered and the solution was concentrated to about 1.5 l under vacuum. The mixture was poured into 7.5 l of ice water and the precipitate formed was filtered off with suction, washed with water and dried over $P_2O_5$.

288.4 g of the title compound (90% of theory, based on d) were obtained. M.p.: 59°–61° C.
$^1$H NMR (300 MHz/TMS/CDCl$_3$)
(ppm) = 2.34 (s, 3H, CH$_3$), 2.47 (s, 3H, CH$_3$), 3.84 (s, 3H, OCH$_3$), 8.32 (s, 1H, pyr-H)

EXAMPLE 4

3,5-Dimethyl-4-methoxy-2-chloromethylpyridine hydrochloride 20 g of 3,5-dimethyl-4-methoxy-2-cyanopyridine were dissolved in 650 ml of NH$_3$-saturated methanol, 20 g of Raney nickel were added under an N$_2$ atmosphere and the mixture was hydrogenated. The catalyst was then filtered off and the solution was evaporated under vacuum.

The residue, consisting of 21.3 g of a violet oil, was dissolved in 100 ml of water and 100 ml of glacial acetic acid, the solution was cooled to 0° C and 25.4 g of NaNO$_2$ in 50 ml of water were added drowise, with cooling. The mixture was then rendered alkaline with 500 ml of 4 N NaOH and about 30 ml of 50% NaOH and extracted with 600 ml of CH$_2$Cl$_2$ and the combined organic phases were dried over Na$_2$SO$_4$.

The dried CH$_2$Cl$_2$ solution was cooled to −10° C. and 50.11 g of SOCl$_2$ were added dropwise. The solution was then evaporated at 45° C. under vacuum and the residue was stirred with i-propanol and filtered off with suction.

11.25 g (41.07% of theory) of the title compound were obtained.
$^1$H NMR (300 MHz/TMS/CDCl$_3$)
(ppm) = 2.46 (s, 3H, CH$_3$), 2.48 (s, 3H. CH$_3$), 4.09 (s, 3H, OCH$_3$), 5.12 (s, 2H, CH$_2$), 8.39 (s, 1H, pyr-H)

What I claim is:
1. 3,5-Dimethyl-4-methoxy-2 aminomethylpyridine.

* * * * *